US00PP35584P3

(12) United States Plant Patent
Schoone

(10) Patent No.: US PP35,584 P3
(45) Date of Patent: Jan. 16, 2024

(54) ***PHALAENOPSIS* PLANT NAMED 'GOOD REASON'**

(50) Latin Name: *Phalaenopsis hybrida*
Varietal Denomination: Good Reason

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/130,914

(22) Filed: Apr. 5, 2023

(65) Prior Publication Data

US 2023/0329132 P1 Oct. 12, 2023

Related U.S. Application Data

(60) Provisional application No. 63/328,154, filed on Apr. 6, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

(56) References Cited

PUBLICATIONS

CPVO Register Version 4.10.10 retrieved on Aug. 10, 2023 at https://online.plantvarieties.eu/publicConsultationDetails?registerId=20220799&denomination=good%20reason, 2 pp. (Year: 2023).*
Floricultura Catalogue 2022 Phalaenopsis, retrieved on Aug. 10, 2023 at https://www.floricultura.com/media/5502/flori_2022_catalogus_phalaenopsis.pdf, cover page and p. 45. (Year: 2022).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'Good Reason', characterized by its broadly upright plant habit; moderately vigorous growth habit; strong flowering stems; strong leaves; freely flowering habit with typically two inflorescences per plant, each inflorescence with numerous flowers; white-colored flowers with conspicuous reddish purple-colored venation with yellow, purplish red and white-colored labellum; and good postproduction longevity.

2 Drawing Sheets

Figure 1:
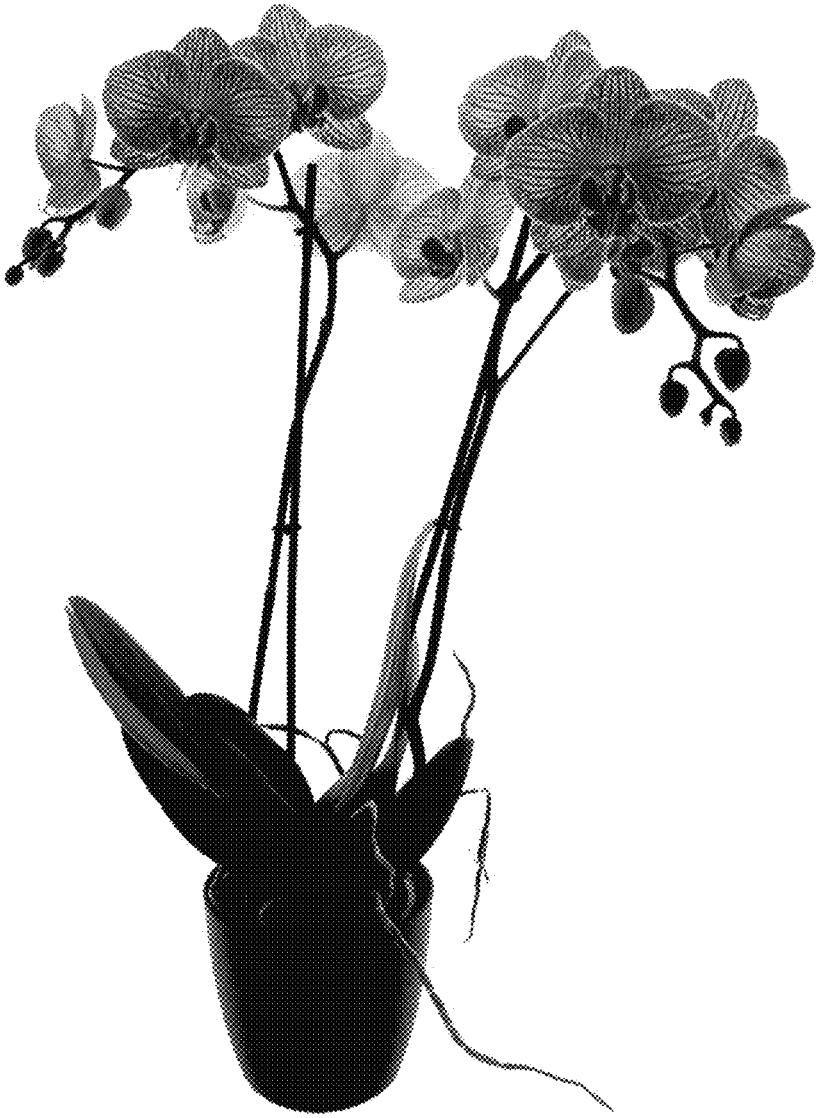

Botanical designation: *Phalaenopsis hybrida.*
Cultivar denomination: 'GOOD REASON'.

CROSS-REFERENCED TO CLOSELY-RELATED APPLICATIONS

An European Community Plant Breeder's Rights application for the instant plant was filed by the Applicant/Assignee of the instant application, Floricultura B.V. of Heemskerk, The Netherlands on Mar. 25, 2022, application number 2022/0799. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Good Reason'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination on Oct. 26, 2012 in Assendelft, The Netherlands of *Phalaenopsis hybrida* 'Black Stripes', not patented, as the female, or seed, parent with *Phalaenopsis hybrida* 'Elegant Wibi Soerjadi', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October, 2018.

Asexual reproduction of the new *Phalaenopsis* plant by in vitro meristem propagation in a controlled environment in Assendelft, The Netherlands since October, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Good Reason'. These characteristics in combination distinguish 'Good Reason' as a new and distinct *Phalaenopsis* plant:

1. Broadly upright plant habit.
2. Moderately vigorous growth habit.
3. Strong flowering stems.
4. Strong leaves.
5. Freely flowering habit with typically two inflorescences per plant, each inflorescence with numerous flowers.
6. White-colored flowers with conspicuous reddish purple-colored venation with yellow, purplish red and white-colored labellum.
7. Good postproduction longevity.

Plants of the new *Phalaenopsis* can be compared to plants of the female parent, 'Black Stripes'. Plants of the new *Phalaenopsis* differ primarily from plants of 'Black Stripes' in flower petal color as petals of plants of the new *Phalaenopsis* have many more stripes and than flower petals of plants of 'Black Stripes'.

Plants of the new *Phalaenopsis* can be compared to plants of the male parent, 'Elegant Wibi Soerjadi'. Plants of the new *Phalaenopsis* differ primarily from plants of 'Elegant Wibi Soerjadi' in flower petal color as flowers of plants of the new *Phalaenopsis* have many more stripes and than flower petals of plants of 'Elegant Wibi Soerjadi'.

Plants of the new *Phalaenopsis* can be compared to plants of *Phalaenopsis hybrida* 'Tropic Picotee', not patented. In side-by-side comparisons, plants of the new *Phalaenopsis* differ primarily from plants of 'Tropic Picotee' in petal curvature as lateral petal lobes of flowers of plants of the new *Phalaenopsis* are slightly curved whereas lateral petal lobes of flowers of plants 'Tropic Picotee' are moderately curved. In addition, the petal shape of flowers of plants of the new *Phalaenopsis* is more compressed than the petal shape of flowers of plants of 'Tropic Picotee'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Good Reason' grown in a container.

Figure 2:
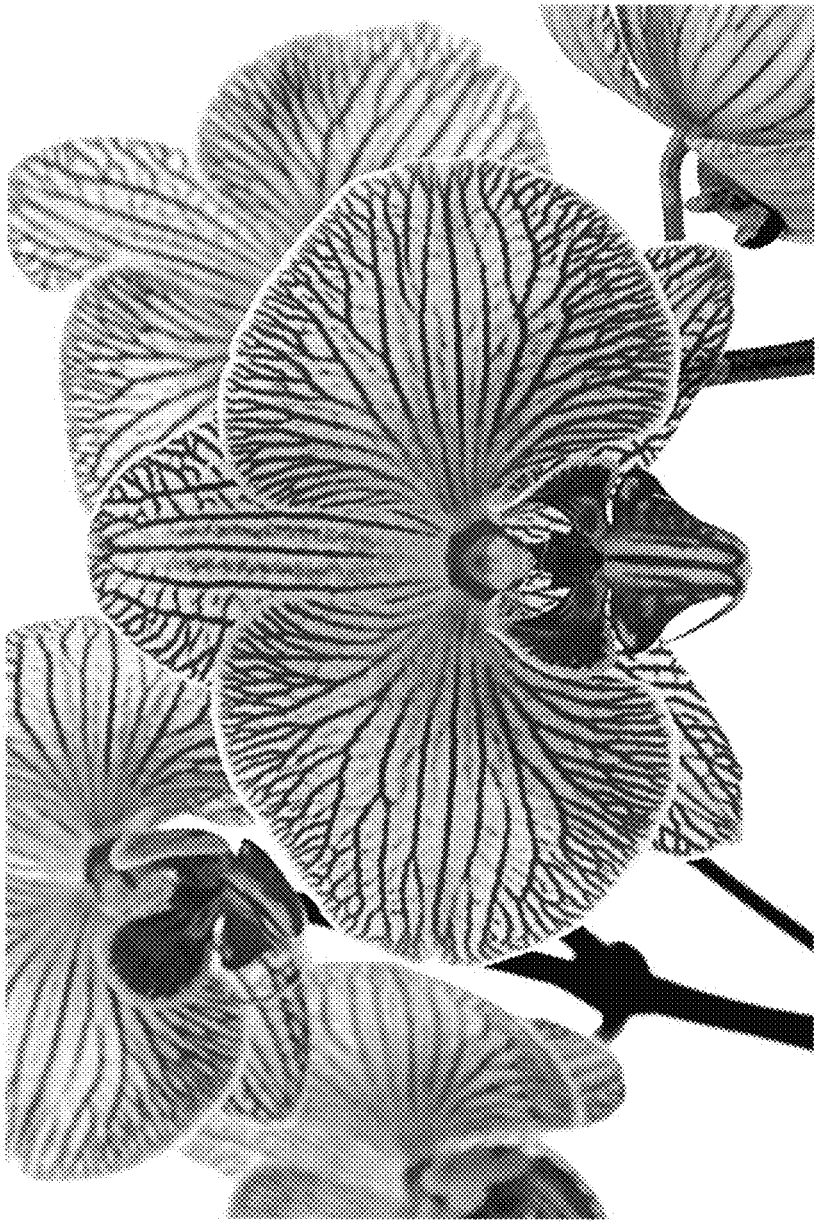

The photograph on the second sheet (FIG. 2) is a close-up view of typical flowers of 'Good Reason'.

DETAILED BOTANICAL DESCRIPTION

The aforementioned photographs and following observations and measurements describe plants grown during the autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20 C to 22 C and night temperatures ranged from 18 C to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Good Reason'.

Parentage:

*Female, or seed, parent.*—*Phalaenopsis hybrida* 'Black Stripes', not patented.

*Male parent.*—*Phalaenopsis hybrida* 'Elegant Wibi Soerjadi', not patented.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; broadly upright plant habit with typically two inflorescences per plant, each inflorescence with numerous flowers; monopodial; moderately vigorous growth habit and moderate growth rate.

*Plant height, substrate level to top of foliar plane.*—About 20 cm.

*Plant height, substrate level to top of inflorescences.*—About 49.3 cm.

*Plant diameter or spread.*—About 29 cm.

Leaf description:

*Arrangement and quantity.*—Distichous, simple; sessile; about five leaves per plant.

*Length.*—About 18.6 cm.

*Width.*—About 7.9 cm.

*Aspect.*—Mostly upright to outwardly arching.

*Shape.*—Narrowly obovate to elliptic-oblong; slightly carinate.

*Apex.*—Unequal obtuse to unequal and broadly acute.

*Base.*—Sheathing. Sheath length: About 1.9 cm. Sheath width: About 1.4 cm. Sheath color: Close to 143B; towards the margins, close to 143A.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to 137A. Developing leaves, lower surface: Close to 146A. Fully expanded leaves, upper surface: Close to NN137B; venation, close to 147A. Fully expanded leaves, lower surface: Close to 146A to 146B; venation, close to 144B.

Inflorescence description:

*Appearance and flowering habit.*—Showy zygomorphic flowers arranged on axillary branched racemes; typically two inflorescences per plant; each inflorescence with about 14 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 27 cm.

*Inflorescence width*.—About 14.7 cm.

*Flower buds*.—Height: About 2.1 cm. Diameter: About 1.5 cm by 1.9 cm. Shape: Broadly ovate. Color: Close to 144C; venation, close to N77B and N77C.

*Flower size*.—About 7.8 cm (vertical) by 9.4 cm (horizontal).

*Flower depth*.—About 3.2 cm.

*Petals, quantity and arrangement*.—Three, two lateral petals and one center petal transformed into a labellum.

*Lateral petals*.—Length: About 4.5 cm. Width: About 5.5 cm. Shape: Roughly reniform to close to lunate. Apex: Obtuse to broadly and shallowly retuse. Margin: Entire. Texture and luster, upper and lower surfaces: Smooth, glabrous, velvety; matte. Color: When opening, upper surface: Close to lighter than NN155D; at the base, close to NN78A; venation, close to N78A; marginal edges (about 1 mm in width) do not have conspicuous venation. When opening, lower surface: Close to NN155C; venation, close to N78A and N78B; marginal edges (about 1 mm in width) do no have conspicuous venation. Fully opened, upper surface: Close to lighter than NN155D; towards the base, close to N75B to N75C and at the base, close to NN78A; venation, close to N78A; marginal edges (about 1 mm in width) do not have conspicuous venation; color does not change with subsequent development. Fully opened, lower surface: Close to NN155C; venation, close to N78A and N78B; marginal edges (about 1 mm in width) do no have conspicuous venation; color does not change with subsequent development.

*Labella*.—Appearance: Three-parted with two lateral lobes and a central lobe. Length, lateral lobes: About 2.2 cm. Width, lateral lobes: About 1.4 cm. Length, central lobe: About 2.1 cm. Width, central lobe: About 7 mm to 21 mm. Length, cirrose tips: About 1.4 cm. Shape, lateral lobes: Obovate. Shape, central lobe: Deltoid with an elongated apex. Apex, lateral lobes: Obtuse. Apex, central lobe: Cleft with two recurved cirrose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4.5 mm in length, about 6 mm in width and about 5 mm in height. Color: When opening, upper surface: Lateral lobes: Close to 75C; towards the upper margin edges, close to N78A; lower margin edges, close to 3A; venation, close to N79C. Central lobe: Close to NN155D with stripes, blotches and venation, close to 64A; towards the upper margin edges, close to NN78A; towards the base of the broad part, blotched and heavily tinged with close to 8C; at the base, close to 75B; radial stripes, close to 59A; cirrose apices, close to NN78A with margins, close to NN155D. Callosities: Close to 13B with fine dots, close to 181A. When opening, lower surface: Lateral lobes: Close to a blend of 75B and 198C; lower margin, close to 5A; towards the base, venation, close to 71B. Central lobe: Close to NN155B; wide parts and margins, densely veined, close to N78A and 78B; at the base, close to 157A and 157B tinged with close to 5C; cirrose apices, close to NN78A with margins, close to NN155D. Fully opened, upper surface: Lateral lobes: Close to 75C; towards the upper margin edges, close to N78A; lower margin edges, close to 12A to 12B; venation, close to N79C. Central lobe: Close to NN155D with stripes, blotches and venation, close to 64A; towards the upper margin edges, close to NN78A; towards the base of the broad part, blotched and heavily tinged with close to 8C; at the base, close to 75B; radial stripes, close to 59A; cirrose apices, close to NN78A with margins, close to NN155D. Callosities: Close to 13A with fine dots, close to 181A. Fully opened, lower surface: Lateral lobes: Close to 76C; lower margin, close to 12B; towards the base, venation, close to 71B. Central lobe: Close to NN155B; wide parts and margins, densely veined, close to N78A and 78B; at the base, close to 157B tinged with close to 5C; cirrose apices, close to NN78A with margins, close to NN155D.

*Sepals*.—Quantity and arrangement: Three, one upper dorsal sepal and two lower lateral sepals. Length, dorsal and lateral sepals: About 4.5 cm. Width, dorsal sepal: About 3.5 cm. Width, lateral sepal: About 2.8 cm. Shape, dorsal sepal: Obovate to broadly elliptic. Shape, lateral sepals: Ovate. Apex, dorsal sepal: Obtuse. Apex, lateral sepals: Bluntly acute. Base, dorsal and lateral sepals: Truncate. Margin, dorsal and lateral sepals: Entire. Texture and luster, dorsal and lateral sepals, upper and lateral surfaces: Smooth, glabrous, moderately velvety; matte. Color, dorsal sepal: When opening, upper surface: Close to lighter than NN155D; at the base, close to NN78A; venation, close to N78A; marginal edges (about 1 mm in width) do not have conspicuous venation. When opening, lower surface: Close to 157A; center, close to 145D; venation, close to N78B; marginal edges (about 1 mm in width) do no have conspicuous venation. Fully opened, upper surface: Close to lighter than NN155D; towards the base, close to N75B to N75C and at the base, close to NN78A; venation, close to N78A; marginal edges (about 1 mm in width) do not have conspicuous venation; color does not change with subsequent development. Fully opened, lower surface: Close to lighter than NN155C; venation, close to N78A and N78B; marginal edges (about 1 mm in width) do no have conspicuous venation; color does not change with subsequent development. Color, lateral sepals: When opening, upper surface: Close 157C to 157D; towards the margins, close to NN155D; at the base, fine dots, close to 71A; venation, close to N78A; marginal edges (about 1 mm in width) do not have conspicuous venation. When opening, lower surface:

Close to 145C; venation, close to N78B; marginal edges (about 1 mm in width) do no have conspicuous venation. Fully opened, upper surface: Close to NN155C; at the base, close to NN78A with fine dots, close to 70A; venation, close to N78A; marginal edges (about 1 mm in width) do not have conspicuous venation; color does not change with subsequent development. Fully opened, lower surface: Close to NN155D; center and towards the base, close to 196A; venation, close to N78C and N78D; marginal edges (about 1 mm in width) do no have conspicuous venation; color does not change with subsequent development.

*Peduncles*.—Length: About 57.3 cm. Diameter: About 5.5 mm. Strength: Strong. Aspect: Upright to outwardly arching. Texture and luster: Smooth, glabrous; matte. Color: Close to a blend of 197A and N200A; densely covered with fine dots and marbling, close to 148B.

*Pedicels*.—Length: About 3.6 cm. Diameter: About 3 mm. Strength: Moderately strong. Aspect: About 50 degrees from peduncle axis. Texture and luster: Smooth, glabrous; matte. Color: Close to N148D; distally, close to 76C to 76D.

*Reproductive organs*.—Androecium: Column length: About 1 cm. Column width: About 6 mm. Column color: Close to N78D; distally, close to NN155D. Pollinia quantity: Two. Pollinia diameter (per two pollinia): About 2.5 mm. Pollinia color: Close to 23A. Gynoecium: Stigma length: About 4 mm. Stigma width: About 5 mm. Stigma shape: Reniform. Stigma color: Close to N155A. Ovary length: About 1 cm. Ovary diameter: About 1 mm. Ovary color: Close to N144B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C and are suitable for USDA Hardiness Zones 10 to 12.

It is claimed:

1. A new and distinct *Phalaenopsis* plant named 'Good Reason' as illustrated and described.

* * * * *